(12) United States Patent
Baram et al.

(10) Patent No.: US 12,161,829 B2
(45) Date of Patent: *Dec. 10, 2024

(54) DEVICE POSITIONABLE IN THE UTERINE CAVITY AND METHOD OF TREATMENT THEREOF

(71) Applicant: OCON MEDICAL LTD., Modiin (IL)

(72) Inventors: Ilan Baram, Giv'ataim (IL); Eran Nir, Rehovot (IL)

(73) Assignee: OCON MEDICAL LTD., Modiin (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,184

(22) Filed: Apr. 26, 2023

(65) Prior Publication Data

US 2023/0338720 A1     Oct. 26, 2023

Related U.S. Application Data

(63) Continuation of application No. 17/575,767, filed on Jan. 14, 2022, now Pat. No. 11,642,502, which is a continuation of application No. PCT/IB2021/058603, filed on Sep. 21, 2021.

(60) Provisional application No. 63/081,028, filed on Sep. 21, 2020.

(51) Int. Cl.
*A61K 33/00* (2006.01)
*A61F 6/14* (2006.01)
*A61K 33/38* (2006.01)
*A61M 31/00* (2006.01)

(52) U.S. Cl.
CPC .......... *A61M 31/002* (2013.01); *A61K 33/00* (2013.01); *A61K 33/38* (2013.01)

(58) Field of Classification Search
CPC ..... A61M 31/002; A61K 33/00; A61K 33/38; A61K 9/0039; A61F 6/142
See application file for complete search history.

(56) References Cited

U.S. PATENT DOCUMENTS

| | | | |
|---|---|---|---|
| 7,419,687 B2 * | 9/2008 | Neuwirth | A61P 15/00 514/495 |
| 10,905,583 B2 * | 2/2021 | Bar-Am | A61F 6/14 |
| 11,642,502 B2 * | 5/2023 | Baram | A61K 33/38 604/288 |

OTHER PUBLICATIONS

Parikh, DM (Handbook of Pharmaceutical Granulation Technology. CRC Press 2016 pp. 78-80 and 83; 3 pages). (Year: 2016).*

* cited by examiner

*Primary Examiner* — Ernst V Arnold
(74) *Attorney, Agent, or Firm* — Greenberg Traurig, LLP

(57) ABSTRACT

A delivery vehicle for a silver ion source such as silver nitrate and the like, suitable for use in the treatment of menorrhagia, comprises a plurality of beads bearing a tissue cauterizing amount of a silver ion source. In some embodiments, the silver ion source is silver nitrate, in combination with a binder of hydroxy propyl cellulose and a diluent of potassium nitrate. In some embodiments, the plurality of beads is useful in treating menorrhagia of a mammalian uterus. Silver ions are delivered in a sufficient amount to the endometrium to cause necrosis of the endometrial tissue.

14 Claims, 8 Drawing Sheets

DEVICE POSITIONABLE IN THE UTERINE CAVITY AND METHOD OF TREATMENT THEREOF

CROSS-REFERENCE TO RELATED APPLICATION

This application is a continuation of U.S. application Ser. No. 17/575,767, filed Jan. 14, 2022, which is a continuation of International Patent Application No. PCT/IB2021/058603 filed Sep. 21, 2021, claiming the benefit of commonly owned U.S. Provisional Patent Application No. 63/081,028, filed on Sep. 21, 2020 and entitled "Device Positionable in the Uterine Cavity and Method of Treatment Thereof," the contents of which are incorporated herein by reference in their entirety.

TECHNICAL FIELD

The present disclosure relates to a device positionable in the uterine cavity and use thereof for treating uterine-related disorders, such as menorrhagia, by delivering tissue necrosing agents.

BACKGROUND

An intrauterine device (IUD) is a small device implanted in the uterine cavity and can be used for birth control and treatment of uterine-related disorders by delivering tissue necrosing agents. Chronic abnormal uterine bleeding (AUB), involving menstrual bleeding of abnormal quantity, duration, frequency, or regularity, is experienced by 10-50% of women of reproductive age, adversely impacts quality of life, and can have substantial adverse economic impacts on patients and healthcare systems. One of AUB's symptoms, heavy menstrual bleeding (HMB), can lead to iron deficiency, iron deficiency anemia, and in acute and severe cases can necessitate emergency medical care. While pharmacologic treatment options exist, they are not always effective, and they are frequently associated with both side effects and ongoing cost of care. For example, a first-line treatment is hormonal treatment using oral contraceptives or a hormonal device. For example, a second-line treatment is global endometrial ablation (GEA), which requires hospitalization and general anesthesia, is invasive, painful, and non-reversible (i.e., infertility).

Consequently, some women desire more definitive options. Endometrial ablation (EA) is a minimally invasive approach designed to manage a number of the causes of HMB and can be performed under direct intrauterine vision with resectoscopic instruments or with a non-resectoscopic approach (non-resectoscopic endometrial ablation or NREA). For NREA, one of a number of specially designed devices is inserted into the endometrial cavity to deliver thermal, cryogenic or radiofrequency electrical energy in an attempt to destroy the uterine lining or endometrium. In some jurisdictions, NREA has become an accepted office-based procedure, but is still usually performed in an institutional setting, is associated with risks associated with the procedure, anesthesia, and subsequent infertility, and has a failure rate that averages about 26%. These devices are typically expensive and require training for both the surgeon and the ancillary support staff.

Silver nitrate ($AgNO_3$) is a colorless to transparent to white crystalline solid with no odor and a bitter metallic taste. A study by Neuwirth, et al. explored the safety, feasibility, and effectiveness of silver nitrate-dextran paste delivered through the cervix as a simple and inexpensive endometrial ablation therapy for menorrhagia. Neuwirth R S, Singer A, Evaluation of a Silver Nitrate Endometrial Ablation Fluid Delivery System as a Chemical Treatment for Menorrhagia, J Minim Invasive Gynecol. September-October 2013; 20(5):627-30. Neuwirth, however, discloses discontinuation of the studies of the silver nitrate-dextran paste delivery system because of the inability to control the locus of caustic action. During the procedure, Neuwirth discloses one patient had silver nitrate paste spill through the left fallopian tube into the peritoneal cavity. Thus, there is a need for safe and effective delivery of tissue necrosing agents to the uterine cavity.

The present invention is a novel, three-dimensional endometrial ablation device and method developed to allow for chemical EA to treat the causes of the symptoms of HMB. The suggested procedure is expected to be simpler than the currently available EA methods and results in a significative improvement in the patient bleeding pattern achieving clinically meaningful delay or abolishment of the need for hysterectomy.

BRIEF DESCRIPTION OF THE INVENTION

In some embodiments, the techniques described herein relate to an intrauterine device including: a wire having a portion capable of forming an elastically deformable three-dimensional structure; wherein the three-dimensional structure: a) is elastically deformable to a partially collapsed configuration; b) has a crush force of at least 15 grams/$cm_2$; and c) is configured to elastically contract and expand in response to contraction and expansion of the uterine cavity, a plurality of beads, including: 80% to 98% by weight of formulated active materials, wherein the formulated active materials include 75% to 100% by weight of silver nitrate and 0% to 25% by weight of potassium nitrate, wherein the ratio of potassium nitrate to silver nitrate is from 1:19 to 1:3, 2% to 20% by weight of a hydroxy propyl cellulose binder; and two fixing beads, each positioned at opposite ends of the wire.

In some embodiments, the techniques described herein relate to a intrauterine device, wherein the plurality of beads is configured to disintegrate and form a paste-like material that spreads and covers a uterine cavity when the plurality of beads is in contact with an endometrial lining of the uterus for a time period sufficient to necrose endometrial tissue.

In some embodiments, the techniques described herein relate to a intrauterine device, wherein the plurality of beads is not physiologically inert.

In some embodiments, the techniques described herein relate to a intrauterine device, wherein the plurality of beads has an overall weight of between 0.6 grams and 1.0 grams.

In some embodiments, the techniques described herein relate to a intrauterine device, wherein each bead including the plurality of beads has a diameter of between 2.2 mm to 3.0 mm.

In some embodiments, the techniques described herein relate to a intrauterine device, wherein the two fixing beads are about 2 mm in diameter.

In some embodiments, the techniques described herein relate to a intrauterine device, wherein the material of the two fixing beads is selected from the group consisting of titanium, gold, and sterling silver.

In some embodiments, the techniques described herein relate to a intrauterine device, wherein the material of the two fixing beads is titanium.

In some embodiments, the techniques described herein relate to a intrauterine device, wherein an Ag+ ion concentration of the silver nitrate is equal to c.a. 0.00334 Mol of Ag+.

In some embodiments, the techniques described herein relate to a intrauterine device, wherein the three-dimensional structure is configured to form two or more contiguous loops of the wire, which are angled with respect to each other.

In some embodiments, the techniques described herein relate to a intrauterine device, wherein the two or more contiguous loops of wire are 12 mm to 18 mm in diameter, respectively.

In some embodiments, the techniques described herein relate to a intrauterine device, wherein the two or more contiguous loops of wire are configured such that one loop is positioned within the plane of the second loop and is angled 60-120 degrees with respect thereto.

In some embodiments, the techniques described herein relate to a intrauterine device, wherein the wire is made of a super elastic material.

In some embodiments, the techniques described herein relate to a intrauterine device, wherein the wire is made of nitinol.

In some embodiments, the techniques described herein relate to a method of treating uterine-related disorders, including the steps of: Administering a plurality of beads to a uterine cavity of a human patient in need including: (i) from 75% to 100% by weight of silver nitrate and 0% to 25% by weight of potassium nitrate; and (ii) from 2% to 20% by weight of a hydroxy propyl cellulose binder; and maintaining the plurality of beads in contact with an endometrial lining of the uterus for a time period sufficient to necrose endometrial tissue.

In some embodiments, the techniques described herein relate to a method, wherein the plurality of beads disintegrate and form a paste-like material that covers the endometrial lining of the uterus for a time period sufficient to necrose endometrial tissue.

BRIEF DESCRIPTION OF THE DRAWINGS

Illustrative examples of the present disclosure are described in detail below with reference to the attached drawing figures, which are incorporated by reference herein, and wherein.

Figure 1:
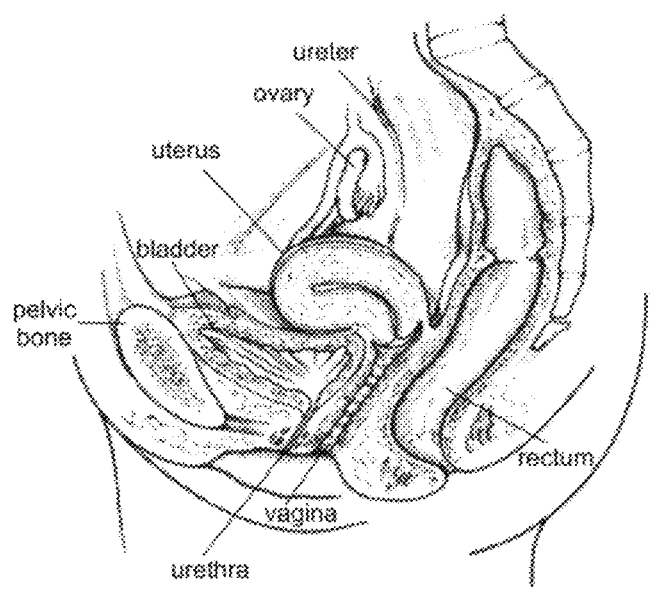
FIG. 1 illustrate a uterine cavity in its relaxed state.

The illustrated figures are exemplary only and are not intended to assert or imply any limitation with regard to the environment, structure, form, design, or process in which different examples may be implemented.

DETAILED DESCRIPTION

In some embodiments, the present invention provides a device and method of treatment suitable for delivering a silver ion source, such as silver nitrate and the like; a potassium source, such as potassium nitrate and the like; and a binder, such as hydroxy propyl cellulose, to the uterine cavity of a patient suffering from menorrhagia to chemically necrose the endometrium. In some embodiments, the device and method of the present invention relates to patients suffering from chronic AUB or HMB, which refers to menstrual bleeding of abnormal quantity, duration, or schedule, a common gynecologic condition, occurring in approximately 10 to 35% of women. Chronic heavy or prolonged uterine bleeding can result in anemia, interfere with daily activities, and raise concerns about uterine cancer.

In some embodiments, the delivery vehicle comprises a plurality of beads bearing a solid silver ion source. In some embodiments, the solid silver ion source adheres firmly to the plurality of beads, but the plurality of beads readily releases a silver ion bearing composition when the plurality of beads come into contact with the moist endometrium of the uterus. In some embodiments, the plurality of beads comprises a composition that is "consumed" or disintegrates after being placed in the uterus—as such, the plurality of beads is not physiologically inert.

In some embodiments, the device contains a plurality of beads having a solid form of silver nitrate and/or silver nitrate and potassium nitrate combined with a soluble binder to keep the components together in a solid form. In some embodiments, once in contact with the endometrium/tissue/uterine fluid, the plurality of beads will disintegrate and form a paste-like material that spreads and covers the uterine cavity. In some embodiments, the viscosity of the paste is such that it flows, but the paste does not spill out of the fallopian tubes or cervical os. The silver nitrate and/or silver nitrate and potassium nitrate will cauterize the tissue (in a self-limiting manner due to its binding to and denaturing proteins) in a more controlled manner. Thus, the risk of spillage through the fallopian tubes, resulting in collateral organ damage, is significantly reduced.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

As used herein "an intrauterine device" refers to any device implantable within the uterine cavity, preferably via delivery through the vaginal cavity and cervix. As is further described herein, such a device is preferably configured for releasing an active agent capable of preventing pregnancy (contraceptive or birth control IUD) or treating a uterine disorder such as menorrhagia or medical or surgical therapy to endometrium or myometrium for any length of time including minutes, hours, days, weeks, months or years.

As used herein the term "about" refers to ±10%.

In its relaxed state, the cavity of the uterus is a mere slit having substantially no volume (FIG. 1). During uterine contractions, the uterine walls relax and contract upon each other. When relaxed, the uterine walls exert an inward force of 10 mmHg (about 13.5 grams cm2), however, under contractions, inward forces exerted by the uterine walls can rise to as much as 50-60 mmHg (about 67-82 grams/cm2) and higher (Gestel et al. Human Reproduction Update, Vol. 9, No. 2 pp. 131-138, 2003).

In some embodiments, there is provided an intrauterine device. In some embodiments, the device includes a wire having a portion capable of forming an elastically deformable three-dimensional structure.

In some embodiments, the wire can be composed of a selected super elastic material capable of being pre-shaped into the three-dimensional structure and being linearized by a pulling force on the ends of the wire. In some embodiments, such a transition between three-dimensional and linear configurations can be effected repeatedly due to the elastic nature of the material and its ability to maintain the three-dimensional shape in the absence of any pulling force on the ends of the wire (e.g., shape memory).

In some embodiments, examples of materials suitable for the wire include, but are not limited to, alloys such as stainless steel, nickel-titanium, copper-aluminum-nickel and other copper containing alloys or polymers such as polyurethanes, polyols, polyethylene terephthalates and acrylates.

In some embodiments, the wire can be 50-100 mm long with the portion forming the three-dimensional structure being 50-100% of the overall length (10-100 mm).

In some embodiments, the three-dimensional structure of the present device is formed by two or more contiguous loops of the wire which are angled with respect to each other. In some embodiments, the loops can be 12-18 mm in diameter and are arranged (in a two loop configuration) such that one loop is positioned within the plane of the second loop and is angled 60-120 degrees, preferably 80-100 degrees, with respect thereto (the angle is measured at the wire portion interconnecting the loops). In some embodiments, thus, the loops form a loop-in-loop structure that 'traps' a roughly spherical volume of 0.9-3.0 cm3 (1-1.5 cm3 preferred) with a surface area of 4.5-10.1 cm2 (6-8 cm2 preferred). Further description of the three-dimensional structure and formation of the loops from the linear/linearized wire is provided hereinbelow.

In some embodiments, the device of the present invention is a three-dimensional spherical frame measuring about 16 mm in diameter and weighing a total of about 1 gram. In some embodiments, the device is constructed with a frame which is made of super elastic nitinol alloy which once deployed from the insertion tube into the uterine cavity coils into a three-dimensional spherical shape. In some embodiments, a thread (e.g., monofilament nylon) is tied through the tip, resulting in two threads, each, for example, 20 to 30 cm in length, for removal of the device. In some embodiments, two fixing beads are threaded and squeezed at opposite ends of the nitinol wire to serve as physical limiters, holding the plurality of silver nitrate and/or silver nitrate and potassium nitrate beads in place.

In some embodiments, the present device was designed in order to improve the stability of a previous design. In order to provide the requisite stability, in some embodiments, the present inventors have uncovered that a wire diameter of 0.3-1.0 mm, preferably 0.4-0.6 mm, combined with a device overall diameter of 12-20 mm result in elastic resistance to wall forces of a relaxed uterus and a slight device shape change under such forces, while enabling the device to contract and expand along with an active uterus (and nearly completely flatten under strong contractions). Although the present device applies a counter force to the relaxed uterine walls, such a counterforce does not result in tissue irritation and does not lead to any discomfort.

In some embodiments, the plurality of beads is substantially spherical in shape and have an average diameter in the range of about 1 to about 6 mm, more preferably about 2 to about 4 mm.

In some embodiments, the plurality of beads is prepared by mixing 90% of formulated active materials (75% silver nitrate and 25% potassium nitrate) with a binder 10% on a weight basis. In some embodiments, this mixture is further dried to form a paste. In some embodiments, the paste is divided into pre-determined size pieces that are molded, using a specially designed mold, into beads. In some embodiments, a uniform size hole is created in each bead. In some embodiments, the plurality of beads is further dried and solidified in an oven.

In some embodiments, the device contains 28 to 32 beads with an overall weight of 0.6 to 1.0 grams. In some embodiments, the overall weight of the plurality of beads is about 0.7 to 0.9 grams. In some embodiments, the overall weight of the plurality of beads is about 0.8 to 0.9 grams. In some embodiments, the individual weight of the plurality of beads is 0.02 to 0.04 grams. In some embodiments, the individual weight of the plurality of beads is 0.03 grams.

In some embodiments, each of the plurality of beads is between about 2 mm to 3 mm in diameter. In some embodiments, each of the plurality of beads is between about 2.1 mm to 2.9 mm in diameter. In some embodiments, each of the plurality of beads is between about 2.2 mm to 2.8 mm in diameter. In some embodiments, each of the plurality of beads is between about 2.3 mm to 2.7 mm in diameter. In some embodiments, each of the plurality of beads is between about 2.4 mm to 2.6 mm in diameter. In some embodiments, each of the plurality of beads is between about 2.7 mm to 2.8 mm in diameter.

In some embodiments, the Ag+ ion concentration is equal to c.a. 0.00334 Mol of Ag+(empirical measurement by titration). In some embodiments, the device contains a plurality of at least 14 beads (average weight 0.8 grams) of the formulated active materials of which 75% (approximately 0.54 grams) is silver nitrate. In some embodiments, the device contains at least 10 to 40 beads. In some embodiments, the device contains a plurality of at least 14 to 36 beads. In some embodiments, the device contains a plurality of at least 18 beads to 32 beads. In some embodiments, the device contains a plurality of at least 22 to 28 beads. In some embodiments, the device contains a plurality of at least 25 beads to 30 beads. In some embodiments, the device contains an average of 0.80 grams of the active materials of which 75% (0.54 grams) is silver nitrate. In some embodiments, the ratio of potassium nitrate to silver nitrate is from 1:19 to 1:3. In some embodiments, the ratio of potassium nitrate to silver nitrate is 1:3.

In some embodiments, the plurality of beads comprises a composition comprising: 90% of formulated active materials (75% silver nitrate and 25% potassium nitrate) and 10% HPC on a weight basis. In some embodiments, the plurality of beads comprises: 80% to 98% of formulated active materials (75% silver nitrate and 25% potassium nitrate) and 2% to 20% HPC on a weight basis. In some embodiments, the plurality of beads comprises: 85% to 93% formulated active materials (75% silver nitrate and 25% potassium nitrate) and 7 to 15% HPC on a weight basis. In some embodiments, the plurality of beads comprises: 88% to 91% formulated active materials (75% silver nitrate and 25% potassium nitrate) and 9% to 12% HPC on a weight basis.

In some embodiments, the plurality of beads comprises a composition comprising: 90% of formulated active materials (80% silver nitrate and 20% potassium nitrate) and 10% HPC on a weight basis. In some embodiments, the plurality of beads comprises: 80% to 98% of formulated active materials (80% silver nitrate and 20% potassium nitrate) and 2% to 20% HPC on a weight basis. In some embodiments, the plurality of beads comprises: 85% to 93% formulated active materials (80% silver nitrate and 20% potassium nitrate) and 7 to 15% HPC on a weight basis. In some embodiments, the plurality of beads comprises: 88% to 91% formulated active materials (80% silver nitrate and 20% potassium nitrate) and 9% to 12% HPC on a weight basis.

In some embodiments, the plurality of beads comprises a composition comprising: 90% of formulated active materials (85% silver nitrate and 15% potassium nitrate) and 10% HPC on a weight basis. In some embodiments, the plurality of beads comprises: 80% to 98% of formulated active materials (85% silver nitrate and 15% potassium nitrate) and 2% to 20% HPC on a weight basis. In some embodiments, the plurality of beads comprises: 85% to 93% formulated active materials (85% silver nitrate and 15% potassium nitrate) and 7 to 15% HPC on a weight basis. In some embodiments, the plurality of beads comprises: 88% to 91% formulated active materials (85% silver nitrate and 15% potassium nitrate) and 9% to 12% HPC on a weight basis.

In some embodiments, the plurality of beads comprises a composition comprising: 90% of formulated active materials (90% silver nitrate and 10% potassium nitrate) and 10% HPC on a weight basis. In some embodiments, the plurality of beads comprises: 80% to 98% of formulated active materials (90% silver nitrate and 10% potassium nitrate) and 2% to 20% HPC on a weight basis. In some embodiments, the plurality of beads comprises: 85% to 93% formulated active materials (90% silver nitrate and 10% potassium nitrate) and 7 to 15% HPC on a weight basis. In some embodiments, the plurality of beads comprises: 88% to 91% formulated active materials (90% silver nitrate and 10% potassium nitrate) and 9% to 12% HPC on a weight basis.

In some embodiments, the plurality of beads comprises a composition comprising: 90% of formulated active materials (95% silver nitrate and 5% potassium nitrate) and 10% HPC on a weight basis. In some embodiments, the plurality of beads comprises: 80% to 98% of formulated active materials (95% silver nitrate and 5% potassium nitrate) and 2% to 20% HPC on a weight basis. In some embodiments, the plurality of beads comprises: 85% to 93% formulated active materials (95% silver nitrate and 5% potassium nitrate) and 7 to 15% HPC on a weight basis. In some embodiments, the plurality of beads comprises: 88% to 91% formulated active materials (95% silver nitrate and 5% potassium nitrate) and 9% to 12% HPC on a weight basis.

In some embodiments, the plurality of beads comprises a composition comprising: 90% of formulated active materials (100% silver nitrate) and 10% HPC on a weight basis. In some embodiments, the plurality of beads comprises: 80% to 98% of formulated active materials (100% silver nitrate) and 2% to 20% HPC on a weight basis. In some embodiments, the plurality of beads comprises: 85% to 93% formulated active materials (100% silver nitrate) and 7 to 15% HPC on a weight basis. In some embodiments, the plurality of beads comprises: 88% to 91% formulated active materials (100% silver nitrate) and 9% to 12% HPC on a weight basis.

In some embodiments, the average inner surface area of the human uterus was calculated to be approximately 12 cm2 based on cavimeter uterine size measurements. In some embodiments, each 1 cm2 of the inner uterine surface will potentially be exposed to about 45.0 mg of silver nitrate. In some embodiments, the device contains approximately 0.0032 moles of Ag+ ions reflecting an average of $2.7 \times 10^{15}$ Ag+ ions. In some embodiments, using the same human uterus inner surface area calculation referred to above, each 1 cm2 is exposed to $2.3 \times 10^{14}$ Ag+ ions.

In some embodiments, the binder or binding agent, is prepared from a solution of 20% w/w hydroxy propyl cellulose (HPC) and 80% w/w ethanol. In some embodiments, HPC is a hydrogel. In some embodiments, HPC has a molecular weight of approximately 100 kD. In some embodiments, HPC has a molecular weight of approximately 60 to 160 kD. In some embodiments, HPC has a molecular weight of approximately 80 to 140 kD. In some embodiments, HPC has a molecular weight of approximately 100 to 120 kD. In some embodiments, HPC improved delivery and provided optimized coverage in the uterine cavity when used as a system, e.g., when used with silver nitrate and potassium nitrate. In an embodiment, the amount of active material in the form of solid silver nitrate beads achieves complete coverage of the entire inner surface of the uterus.

In some embodiments, each of the plurality of beads has the same geometry. In some embodiments, one or more of the plurality of beads has a different geometry. In some embodiments, each of the plurality of beads may be any conventional bead shape including, but not limited to, sphere, cylinder, cone, regular polyhedron, irregular polyhedron, or other suitable geometry to achieve the desired contraceptive or treatment outcome disclosed herein.

In some embodiments, the plurality of beads can be threaded or slidably mounted over the wire and freely move thereon in which case the plurality of beads include a central through-hole (0.4-1.1 mm in diameter), and/or they can be fixedly attached to the wire via an adhesive, or crimping. In some embodiments, the plurality of beads are threaded over a nitinol wire frame and remain on the frame by using two fixing beads. In some embodiments, examples of materials suitable for the fixing beads include, but are not limited to, titanium, gold, and sterling silver.

In some embodiments, the fixing beads are between 1 mm and 3 mm in diameter. In some embodiments, the fixing beads are about 2 mm in diameter. In some embodiments, the fixing beads have the same geometry. In some embodiments, the fixing beads each has a different geometry. In some embodiments, the fixing beads may be any conventional bead shape including, but not limited to, sphere, cylinder, cone, regular polyhedron, irregular polyhedron, or other suitable geometry to achieve the desired contraceptive or treatment outcome disclosed herein.

Figure 4:
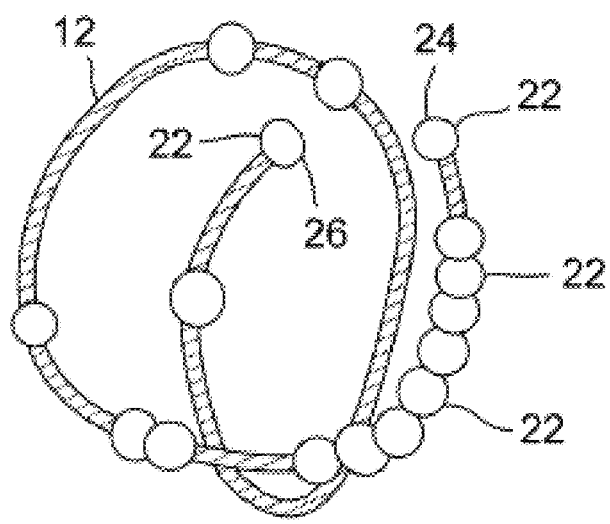
FIG. 4 illustrates, in some embodiments, a configuration of the device of FIG. 2 which includes a plurality of beads disposed on the wire.

In some embodiments, a monofilament nylon removal thread is tied to the end of the frame. A configuration of the present device which includes fixed and freely moving beads is illustrated in FIG. 4, which is described in greater detail below.

Figure 2:
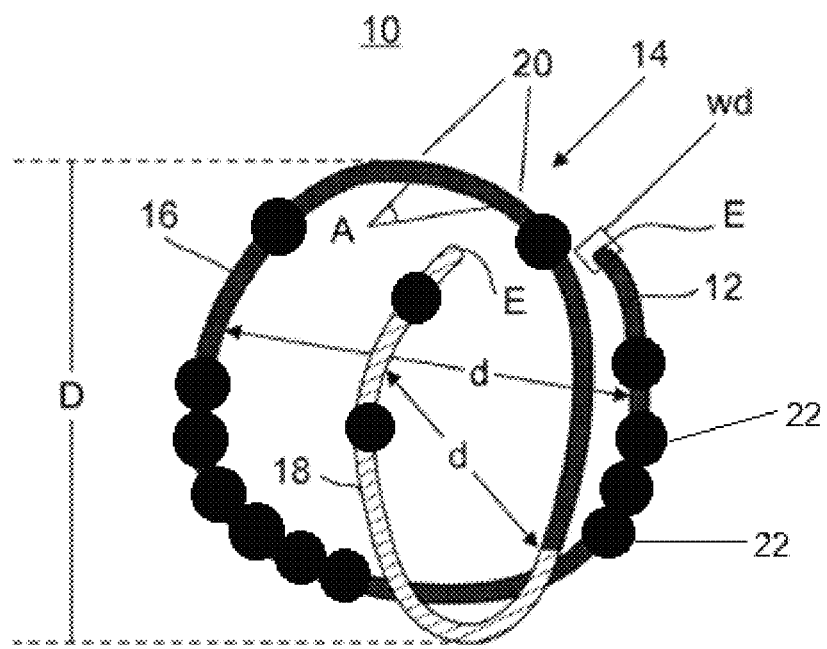
FIG. 2 illustrates, in some embodiments, the present device in its three-dimensional configuration.

Referring now to the drawings, FIG. 2 illustrates one embodiment of the present device which is referred to herein as device 10.

Figure 3:
FIG. 3 illustrates, in some embodiments, the device of FIG. 2 partially compressed by the forces of the relaxed uterine walls.

Device 10 includes a wire 12, which has beads 22 disposed over the wire 12, forming a three-dimensional structure 14 from a first loop 16 contiguous with a second loop 18. The ends of wire 12 (indicated by E) are turned inward in the direction of the volume defined by loops 16 and 18 of device 10. To illustrate the ends of the wire 12 (indicated by E) fixing beads 24 and 26 (FIG. 4) are not pictured. Any of ends E can be connected to a pull string 57 (FIGS. 3 and 5) for loading device 10 into a delivery guide (not pictured) and for removing device 10 from the body. Such a pull string can be fabricated from nylon, polypropylene or polyethylene attached to wire 12 via gluing crimping etc. The function of pull string 57 is described hereinbelow.

Loops 16 and 18 are connected via a contiguous segment 20 which forms an angle 'A' between loops 16 and 18; angle 'A' can be 80-100 degrees.

The overall diameter of device 10 (D) can be 12-15 mm, preferably 13 mm. Loops 16 and 18 are substantially of equal diameter (d) of 12-18 mm, preferably 13 mm. The diameter of wire 12 (wd) can be 0.4-1.0 mm, preferably 0.6 mm.

As is mentioned hereinabove, device 10 is configured to partially compress under the forces applied by the walls of a relaxed uterine cavity.

For example, a device 10 having an overall diameter of 13 mm constructed from a Nitinol wire (0.5 mm in diameter) formed into two contiguous loops (13 mm in diameter) an angled at 90 degrees with respect to each other would partially collapse under a force of 13.6 grams/cm2 to form a roughly oval shape (FIG. 3) with a height of 10 mm. When partially collapsed, device 10 applies an elastic counterforce to the walls of the uterine cavity thus firmly securing device 10 in position. Near flattening of this configuration of device 10 would require about 50-60 grams/cm2.

Collapse of device 10 under such forces is influenced by two separate or combined mechanisms, change in angle A (elastic bending at segment 20) and shape change (round to oval) in each of loops 16 and 18 (elastic bending of the loops).

Collapse along one axis of device 10 is primarily mediated by segment 20 which can bend under relatively lower forces (exerted by relaxed uterine walls). Such collapse enables device 10 to assume the oval-shaped configuration described above. Collapse along other axis requires a larger force (uterine contractions) since it necessitates a shape-change (round to oval) in loops 16 and 18 (as well as further bending of segment 20).

Collapse through a combination of axis is also possible and will depend on the orientation of device 10 in the uterine cavity and type of contractions.

FIG. 4 illustrates a configuration of device 10 which includes a plurality of beads 22 disposed over wire 12. As is mentioned hereinabove, plurality of beads 22 can be fixed to, and/or they can freely move upon wire 12. In the configuration shown in FIG. 4, fixing beads 24 and 26 are fixed to ends of wire 12, while the plurality of beads 22 in-between freely moves along wire 12.

Fixing beads 24 and 26 while allowing the plurality of beads 22 (in-between beads 24 and 26) to freely slide upon wire 12 may provide several advantages. Fixing beads 24 and 26 protect (and blunt) the ends of wire 12 thus minimizing the chances of tissue perforation during delivery and precludes any sharp edges from irritating or piercing tissue during the course of use.

Allowing the plurality of beads 22 (in-between beads 24 and 26) to freely slide on wire 12 may optimize contact between the plurality of beads 22 and the uterine wall thus maximizing contact between the active agent contained therein and the tissue wall as well as reducing potential irritation that may be caused by a stationary bead during the course of use.

Device 10 can be fabricated by winding a wire (e.g., nitinol) around a mold (e.g., mandrel) capable of maintaining the wire in the desired form. The mold and wound wire are then heated or chemically treated for a specified time to set the wire in the molded shape and the shaped wire is removed from the mold. The formed wire structure can then be coated and/or beads can be threaded thereupon with a leading and trailing bead permanently attached to the wire via soldering. Any excess wire protruding past the leading or trailing bead can then be trimmed.

Delivery and implantation of device 10 in the uterine cavity is preferably carried out using a dedicated delivery guide.

Figure 5:
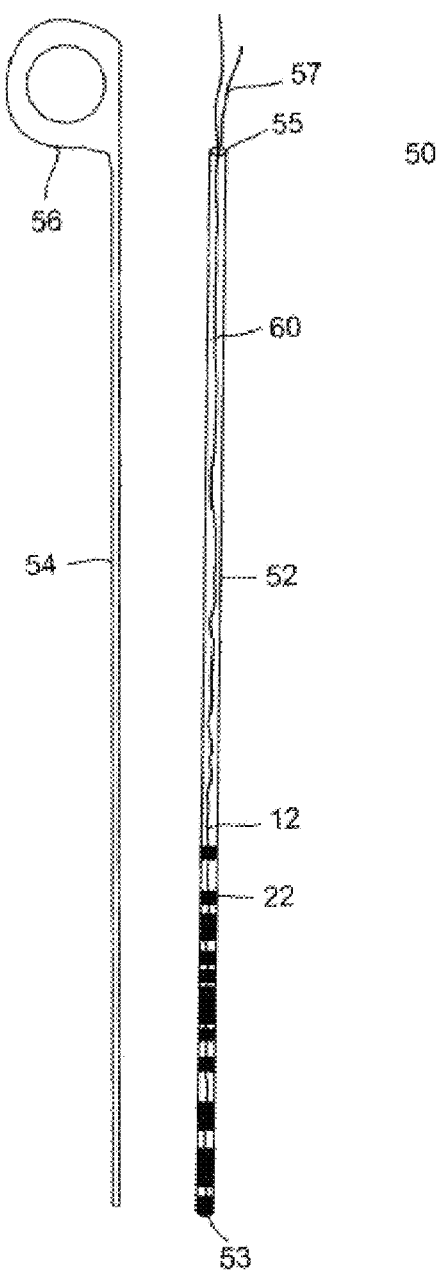
FIG. 5 illustrates, in some embodiments, a delivery guide utilizable for delivering the present device into a uterine cavity.

FIG. 5 illustrates one configuration of such a delivery guide which is referred to herein as guide 50.

Guide 50 includes a hollow tube 52 having a distal opening 53 and a proximal opening 55 defining a lumen therebetween. Wire 12 with a mounted plurality of beads 22 and attached pull string 57 is linearized and positioned within the lumen of tube 52. Device 10 can be loaded into the lumen by threading pull string 57 into lumen and pulling it through thereby linearizing the three-dimensional structure formed by wire 12 as it is pulled into the lumen. A typical pulling force required for such linearization can be 100-150 grams.

Guide 50 also includes a plunger 54 having a shaft 58 fitted with a handle 56. Plunger shaft 58 fits into the lumen of tube 52 through proximal opening 55. Handle 56 is used to advance shaft 58 within the lumen of tube 52 thus advancing wire 12 with a plurality of fitted beads 22 out of distal opening 53 incrementally forming the two-loop three-dimensional structure of the present device.

Figure 6A:
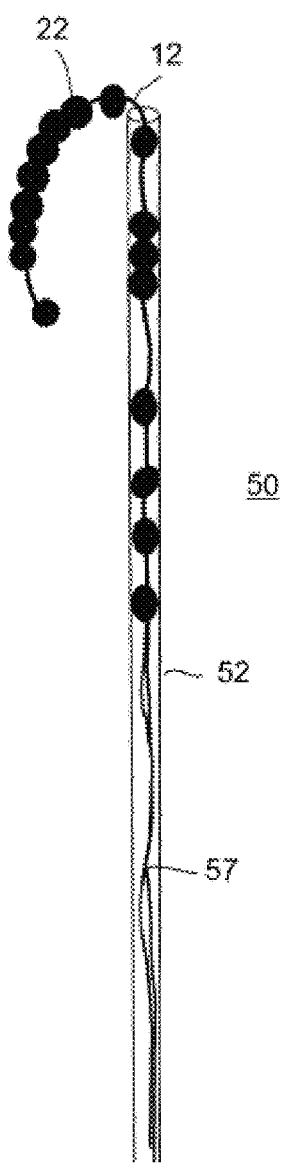
FIG. 6a-c illustrate, in some embodiments, stepwise formation of the three-dimensional structure of the present device as it is pushed out of the delivery guide in the uterine cavity.
Figure 6B:
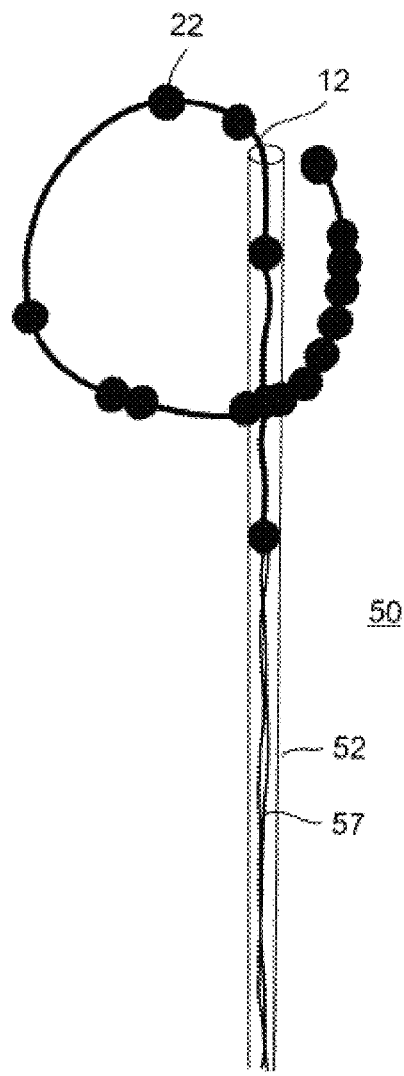
Figure 6C:
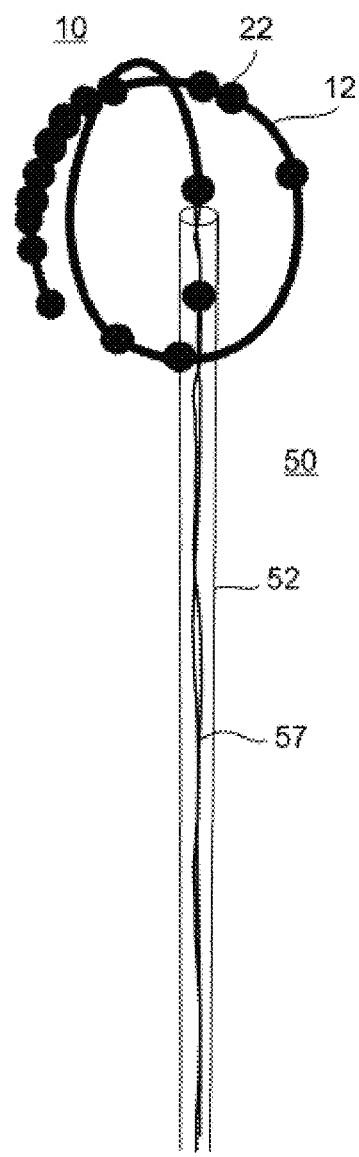

FIGS. 6a-c illustrate delivery of device 10 into a uterine cavity using delivery guide 50.

Distal opening 53 (not shown in FIGS. 6a-c) of guide 50 is positionable in the uterine cavity by measuring uterine depth prior to insertion using a hysterometer (sound). The measured depth from the fundus to the external ostium of the cervical canal is determined by adjusting a slider or flange to the desired length of the tube. In some embodiments, the measured depth from the fundus to the external ostium of the cervical canal is marked on tube 52 as reference to the insertion depth of guide 50.

Plunger 54 (FIG. 5) is then used to advance wire 12 and attached plurality of beads 22 out of distal opening 53 (FIG. 5) as is shown in FIGS. 6a-c, thereby forming the first loop (FIG. 6b) and contiguous second loop (FIG. 6c) of the 3D structure of device 10 from the linear wire. Delivery guide 50 is then removed from the body leaving behind device 10 in the uterus and attached pull string 57, the proximal end of which is positioned at the vaginal canal.

Delivery guide 50 can also include an attached light source (e.g., LED or fiber optic light) in order to illuminate the uterine cavity with white light or light of a specific wavelength (e.g., blue light). Delivery guide can also include a camera for imaging the uterine cavity in 3D instead of using a hysteroscope.

In some embodiments, a method of treating menorrhagia is disclosed comprising the steps of administering to the uterine cavity of a patient suffering from menorrhagia a plurality of beads bearing a tissue cauterizing amount of a solid silver ion source such as silver nitrate and the like; and maintaining the plurality of beads in contact with the endometrial lining of the uterus for a time period sufficient to necrose the endometrial tissue.

In some embodiments, the method of treatment of the present invention reduces one or more of the following indications: intrauterine treatment of disorganized proliferative (benign) endometrial conditions resulting in AUB; intrauterine treatment of menorrhagia (menstrual periods with abnormally heavy or prolonged bleeding) and metrorrhagia (irregular bleeding); and/or intrauterine treatment of Endometrial Hyperplasia.

In some embodiments, the device and method of treatment of the present invention causes local tissue cauterization of the endometrium by utilizing the cauterization properties of a solid form of the caustic agent silver nitrate. Once deployed from the insertion tube, the plurality of beads disintegrates, spread in the uterine cavity and chemically ablate the endometrium upon direct contact. In some embodiments, following 30 minutes of treatment, the device is removed from the uterine cavity by the attached removal threads. In some embodiments, following 20 minutes of treatment, the device is removed from the uterine cavity by the attached removal threads. In some embodiments, following 25 minutes of treatment, the device is removed from the uterine cavity by the attached removal threads. In some embodiments, following 35 minutes of treatment, the device is removed from the uterine cavity by the attached removal threads. In some embodiments, following 40 minutes of treatment, the device is removed from the uterine cavity by the attached removal threads. In some embodiments, following 45 minutes of treatment, the device is removed from the uterine cavity by the attached removal threads. In some embodiments, after the device is removed from the uterine cavity, the cervix is washed with saline solution. In some embodiments, the saline solution contains 0.9 w/v % of chlorine ions. Any remaining silver ions become inactive after contacting with the endometrial tissue, uterine fluid and body exudates, which are rich in chlorine ions. The formed complex deactivates the silver ion resulting in silver chloride, a non-dissolvable salt, that will be washed out in a few days or with the next menses.

In some embodiments, the method of treatment comprises the steps of: deploying the device within the uterine cavity environment, resuming the device predetermined three-dimensional spherical shape, and maintaining the device within the uterine cavity so the plurality of beads disintegrates in the uterus resulting in the silver nitrate coming in contact with the uterine endometrium tissue and resulting in cauterization of the uterine endometrium tissue. One advantage of the present invention is that the silver nitrate cauterization mechanism is self-limiting because the silver ions oxidize tissue proteins to silver-proteinate which then reacts with chlorides and sulfides to form dark colored, inactive, insoluble compounds (colorants). As such, the silver nitrate becomes inactive within 2 to 50 minutes (e.g., 5 to 45 minutes, 10 to 40 minutes, 15 to 35 minutes or 20 to 30 minutes), so that when the device is removed no active material remains in the subject's uterus.

In some embodiments, the method of treatment comprises the following steps:
   measuring the uterine depth of a patient;
   marking the distance with a flange from the top of a loaded insertion tube, wherein the device is contained within the loaded insertion tube, as the uterine depth of the patient;
   passing the loaded insertion tube through the cervical canal of the patient until the flange reaches the outer cervical opening so that the tip of the insertion tube is touching the uterine fundus;
   pulling back the insertion tube 3-5 mm;
   releasing the device into the uterine cavity by holding the insertion tube without pulling the insertion tube out and pushing a rod all the way into the uterine cavity;
   removing the rod and the insertion tube; and
   removing the device after X minutes (wherein X is about 15 to 45 minutes).

Additional objects, advantages, and novel features of the present invention will become apparent to one ordinarily skilled in the art upon examination of the following examples, which are not intended to be limiting.

EXAMPLES

The present disclosure can be better understood by reference to the following examples, which are offered by way of illustration. The present disclosure is not limited to the examples given herein.

Example 1

The device contains a plurality of beads. This example discloses the preparation of the plurality of beads having a solid form of formulated active materials (i.e., salt components) combined with a soluble binder. In this example, 90% of formulated active materials are combined with 10% of a binder on a weight basis. The binder or binding agent, is prepared from a solution of 20% w/w hydroxy propyl cellulose (HPC) and 80% w/w ethanol. Thus, the starting materials are 90% w/w salt components, 2% w/w HPC and 8% w/w ethanol. The binder solution is prepared and conditioned for 2-3 days before mixture with the formulated active materials. The binder solution is dried at 70 to 80° C. to evaporate the ethanol to result in the final HPC binder. In this example, after complete drying, 2.2% w/w HPC and 97.8% w/w salt components are present.

Example 2

A phase I clinical study, recruiting up to 10 women, was designed to evaluate the safety and efficacy of device disclosed herein. The subjects were scheduled to undergo hysterectomy due to AUB of benign causes, who failed or could not tolerate medical therapy (1st line) or who preferred treatment options not requiring frequent dosing. The investigational treatment involved a thirty minute endometrial ablation session using the device, executed in the operating room, immediately followed by the planned hysterectomy procedure.

Efforts were made to recruit an equal number of women with high endometrial thickness (>7 mm) and low endometrial thickness (<7 mm). On the day of surgery, the subject underwent a vaginal ultrasound, to re-measure the endometrial thickness, and hysteroscopy, to visualize the uterine cavity and the endometrium. The device was inserted, under general anesthesia and under uterine visualization, into the uterine cavity via the vagina, and left in the uterus for 30 minutes. The device was removed via the vagina and while the cervix was flushed with normal saline. Once the device was removed, the planned surgical hysterectomy was performed.

After surgery, the extracted uterus was immediately evaluated by the study pathologist for gross pathology and silver nitrate coverage of the endometrium and was later subjected to pathology (macroscopic analyses of the intrauterine cavity and microscopic analyses of the multiple sections of the uteri) histopathological evaluations to define the extent of active material endometrium coverage and endometrial ablation.

Macroscopic pathological analysis of the uteri demonstrated intense staining of the endometrium by silver nitrate, with a high degree of coverage. No staining of the fallopian tubes was reported. Microscopic evaluations were conducted by a certified human pathologist, using a systematic approach of creating blocks and hematoxylin & eosine stained slides from different areas of the uterus. The specimens demonstrated extensive denuding of the superficial-functional layer of the endometrium, with sloughing into the uterine cavity. The remaining superficial-functionalis layer showed varying degrees of detachment, disintegration of glands, congestion and hemorrhage. The depth and extent of damage varied across the tissue within and between patients. The basalis layer had various degrees of disrupted glands, dilated and congested blood vessels and hemorrhages. High variability in the depth and extent of damage to the basalis layer was observed in the same patient and between patients.

Several cases of small "crater-like areas" where the endometrium was absent, were reported. In most cases, the superficial myometrium contained dilated and mildly congested blood vessels, with no tissue damage.

There was a strong correlation between localization of the silver nitrate and observed damage. The cervix showed superficial silver nitrate staining, with no damage to the columnar epithelium and no pathological findings. Histological analysis showed no damage to either the cervical canal, vagina, or the internal organs. No spillage via the fallopian tubes was reported. A strong correlation was noted between localization of the silver nitrate and observed damage to the targeted endometrium, with the degree of damage varying between the subjects and the different uterine section. In all patients, following macroscopic evaluation, silver nitrate was demonstrated in the entire uterine cavity, covering the entire endometrium. Taken together, silver nitrate elicited the expected cauterization effect.

Example 3

A Phase IIA randomized, perspective pre-pivotal study was designed to assess the safety and performance of the device disclosed herein and the ablation procedure. The study was performed in an outpatient setting in women suffering from AUB, with follow up for 12 months post-treatment. The subjects underwent a 30-min endometrial ablation session using the device disclosed herein, in a hospital outpatient clinic. There were two cohorts. Cohort I comprised women experiencing a sub-optimal treatment response (at least 3 months and no later than 12 months after the first treatment) who were eligible to receive a second treatment using the device disclosed herein. Cohort II comprised women who underwent a second treatment session within 7 days following cessation of their next menses or, in cases where menstruation could not be defined, 28-29 days following the first treatment session. The patients were randomized to cohort I and cohort II. The average patient age was 42 years, average baseline Pictorial Blood Loss Assessment Chart (PBAC) was 541 and quality of life (QoL) (measured by Short Form 12 (SF12)) was 39.

The device used in the Phase IIA trial was a three-dimensional spherical frame measuring about 16 mm in diameter and weighing a total of about 1 gram. It is comprised of a super elastic memory shaped nitinol alloy frame which, once deployed from the insertion tube into the uterine cavity, coils into a three-dimensional spherical shape. A monofilament nylon thread is tied through the tip, resulting in two threads, each 20-30 cm in length, for removal of the device. Thirty (30) solid spherical shaped silver nitrate beads, each 3 mm in diameter weighing together an average of 0.81 grams, are threaded over the device frame in free motion. Two titanium beads (2 mm in diameter) are threaded and squeezed at both ends of the nitinol wire to serve as physical limiters to prevent the silver nitrate cylinders from falling off.

The preliminary results showing a PBAC comparison between baseline and 6 months post-treatment is available, which is presented in Table 1.

TABLE 1

| Patient | PBAC Baseline | PBAC at 6 Months | % reduction |
|---------|---------------|------------------|-------------|
| 01-003  | 602           | 536              | 11%         |
| 01-002  | 201           | 83               | 59%         |
| 01-010  | 214           | 14               | 93%         |
| 01-008  | 593           | 18               | 97%         |
| 01-007  | 332           | 0                | 100%        |
| 02-006  | 510           | 26               | 95%         |
| 02-008  | 254           | 2                | 99%         |
| 02-002  | 500           | 111              | 78%         |
| 02-009  | 382           | 112              | 71%         |
| 01-011  | 420           | 58               | 86%         |
| 02-013  | 672           | 90               | 87%         |
| 02-014  | 246           | 31               | 87%         |
| 02-016  | 672           | 140              | 79%         |
| 02-020  | 331           | 20               | 94%         |
| Average | 424           | 89               | 81%         |

To date, no major safety issues have been raised.

One or more illustrative examples incorporating the examples disclosed herein are presented. Not all features of a physical implementation are described or shown in this application for the sake of clarity. Therefore, the disclosed systems and methods are well adapted to attain the ends and advantages mentioned, as well as those that are inherent therein. The particular examples disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown other than as described in the claims below. It is therefore evident that the particular illustrative examples disclosed above may be altered, combined, or modified, and all such variations are considered within the scope of the present disclosure. The systems and methods illustratively disclosed herein may suitably be practiced in the absence of any element that is not specifically disclosed herein and/or any optional element disclosed herein.

Although the present disclosure and its advantages have been described in detail, it should be understood that various changes, substitutions and alterations can be made herein without departing from the spirit and scope of the disclosure as defined by the following claims.

What is claimed is:

1. An intrauterine device comprising:
a wire having a portion capable of forming an elastically deformable three-dimensional structure;
   wherein the three-dimensional structure:
      a) is elastically deformable to a partially collapsed configuration;
      b) has a crush force of at least 15 grams/cm$^2$; and
      c) is configured to elastically contract and expand in response to contraction and expansion of the uterine cavity,
a plurality of beads, comprising:
   80% to 98% by weight of formulated active materials, wherein the formulated active materials comprise 75% to 100%
      by weight of silver nitrate and 0% to 25% by weight of potassium nitrate,
     wherein the ratio of potassium nitrate to silver nitrate is from 1:19 to 1:3, and
   2% to 20% by weight of a hydroxy propyl cellulose binder; and
two fixing beads, each positioned at opposite ends of the wire.

2. The intrauterine device of claim 1, wherein the plurality of beads is configured to disintegrate and form a paste material that spreads and covers a uterine cavity when the plurality of beads is in contact with an endometrial lining of the uterus for a time period sufficient to necrose endometrial tissue.

3. The intrauterine device of claim 1, wherein the plurality of beads is not physiologically inert.

4. The intrauterine device of claim 1, wherein the plurality of beads has an overall weight of between 0.6 grams and 1.0 grams.

5. The intrauterine device of claim 1, wherein each bead of the plurality of beads has a diameter of between 2.2 mm to 3.0 mm.

6. The intrauterine device of claim 1, wherein the two fixing beads are about 2 mm in diameter.

7. The intrauterine device of claim 6, wherein the material of the two fixing beads is selected from the group consisting of titanium, gold, and sterling silver.

8. The intrauterine device of claim 7, wherein the material of the two fixing beads is titanium.

9. The intrauterine device of claim 1, wherein an $Ag^+$ ion concentration of the silver nitrate is equal to c.a. 0.00334 Mol of $Ag^+$.

10. The intrauterine device of claim 1, wherein the three-dimensional structure is configured to form two or more contiguous loops of the wire, which are angled with respect to each other.

11. The intrauterine device of claim 10, wherein the two or more contiguous loops of wire are 12 mm to 18 mm in diameter, respectively.

12. The intrauterine device of claim 10, wherein the two or more contiguous loops of wire are configured such that one loop is positioned within the plane of the second loop and is angled 60-120 degrees with respect thereto.

13. The intrauterine device of claim 1, wherein the wire is made of a super elastic material.

14. The intrauterine device of claim 13, wherein the wire is made of nitinol.

* * * * *